United States Patent [19]
Bowles et al.

[11] Patent Number: 5,594,770
[45] Date of Patent: Jan. 14, 1997

[54] METHOD AND APPARATUS FOR IMAGING OBSCURED AREAS OF A TEST OBJECT

[75] Inventors: Philip Bowles, Carmel, Ind.; Eric Duff; Dale D. Thayer, both of San Diego, Calif.

[73] Assignee: ThermoSpectra Corporation, Franklin, Mass.

[21] Appl. No.: 342,928

[22] Filed: Nov. 18, 1994

[51] Int. Cl.⁶ .................................................. G01B 15/06
[52] U.S. Cl. .............................. 378/58; 378/4; 378/98.6
[58] Field of Search .................... 378/57, 58, 4, 378/62, 98.2, 24, 25, 27, 21, 22, 11, 98.6

[56] References Cited

U.S. PATENT DOCUMENTS

| | | | |
|---|---|---|---|
| 4,809,308 | 2/1989 | Adams et al. | 378/58 |
| 4,926,452 | 5/1990 | Baker et al. | 378/113 |
| 5,020,086 | 5/1991 | Peugeot | 378/113 |
| 5,081,656 | 1/1992 | Baker et al. | 378/21 |
| 5,097,492 | 3/1992 | Baker et al. | 378/22 |
| 5,138,642 | 8/1992 | McCroskey et al. | 378/19 |
| 5,199,054 | 3/1993 | Adams et al. | 378/21 |
| 5,259,012 | 11/1993 | Baker et al. | 378/21 |
| 5,291,535 | 3/1994 | Baker et al. | 378/22 |

*Primary Examiner*—Don Wong
*Attorney, Agent, or Firm*—Banner & Witcoff, Ltd.

[57] ABSTRACT

A method and apparatus are provided for imaging obscured areas of a test object. The apparatus includes an x-ray source having a cathode for producing a steerable electron beam. A controller directs the electron beam to predetermined locations on a target anode. The user may flexibly select appropriate predetermined positions. The predetermined locations may be obtained from the geometry of an obscuration. A detector receives x-rays that are transmitted through the test object from each of the predetermined locations, and produces images corresponding to each of the predetermined locations. The images are digitized and may be combined to produce an unobscured image of a region of interest.

60 Claims, 6 Drawing Sheets

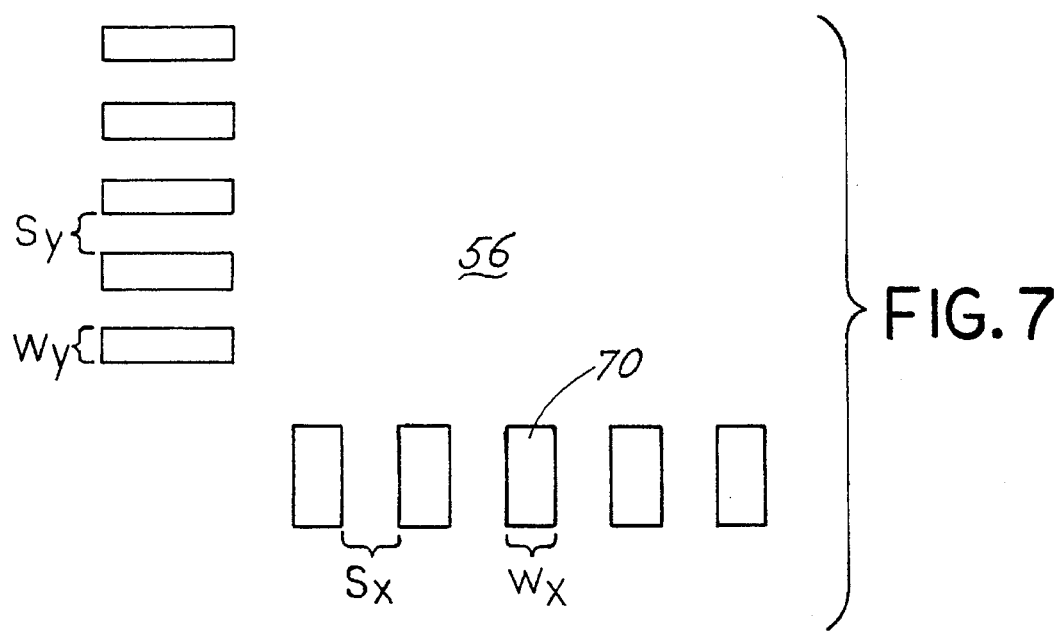
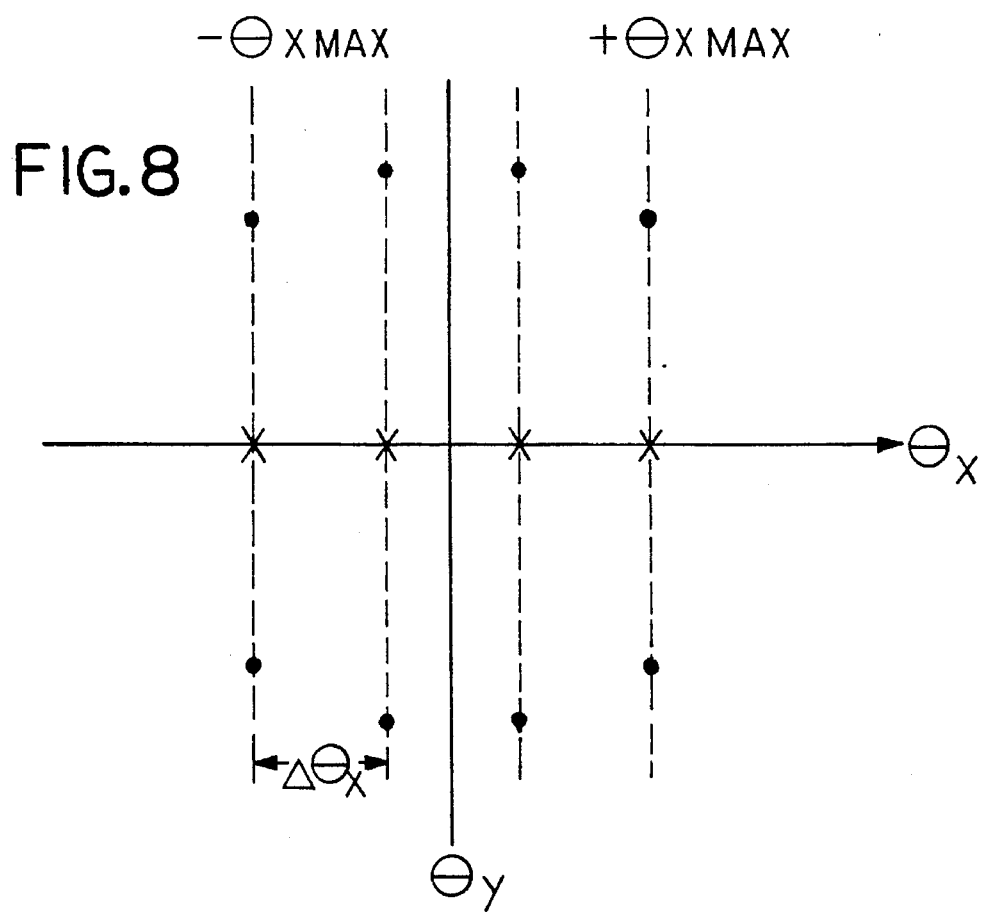

METHOD AND APPARATUS FOR IMAGING OBSCURED AREAS OF A TEST OBJECT

BACKGROUND OF THE INVENTION

The present invention relates to imaging inspection systems and techniques. More specifically, the present invention relates to a novel method and apparatus for imaging obscured areas of a test object.

In the field of automatic inspection devices, systems are known that are capable of providing diagnostic information, whether qualitative or quantitative, about a region of interest. In certain applications, such as the inspection of printed circuit boards ("PCBs"), the region of interest may lie in a particular plane within or on the surface of an object being inspected. It is therefore desirable to extract the diagnostic information from the plane containing the region of interest while ignoring information produced by artifacts or substances lying outside the region of interest. The present invention relates to systems and techniques used to produce a representation of a two-dimensional plane passing through a three-dimensional test object.

An automatic inspection device that is capable of providing diagnostic information from the plane containing the region of interest within or on the surface of the test object is shown, for example, in U.S. Pat. No. 5,097,492 issued to Baker et al. Baker shows an automated laminography system for the inspection of electronics. An electron beam within an x-ray source is deflected to scan a circular pattern on a target anode. An x-ray detector is rotated in synchronization with the deflection of the electron beam to intercept x-rays transmitted through the region of interest within the test object. The inspection device produces a laminographic cross-sectional image.

A disadvantage of the Baker device is that the detector is rotated in synchronization with the steering of the electron beam, requiring precise mechanical control of the detector position as well as increased mechanical complexity. Formation of a high resolution laminographic cross-sectional image depends upon the precise alignment and synchronization of the circular motions of the x-ray source and detector. A further disadvantage of the Baker device is that blurred information may mask diagnostic information, particularly where x-ray opaque substances are located above or below the region of interest. A still further disadvantage of the Baker device is that the circular acquisition geometry of the source and detector may not provide a sufficient representation of the region of interest for all PCBs.

Accordingly, it would be desirable to have an improved method and apparatus for imaging obscured devices.

SUMMARY OF THE INVENTION

According to a first aspect of the present invention, an apparatus for imaging an obscured region of interest is provided. The apparatus includes an x-ray source having a cathode for producing a steerable electron beam. A controller directs the electron beam to predetermined locations on a target anode. The predetermined locations may be obtained from the geometry of an obscuration. A detector receives x-rays that are transmitted through the test object from each of the predetermined locations, and produces images corresponding to each of the predetermined locations. The images are digitized and may be combined to produce an unobscured image of a region of interest.

According to a second aspect of the present invention, a method of imaging an obscured region of interest is provided. The method includes generating an electron beam, and directing the electron beam to predetermined locations on a target. For each of the predetermined locations, the method includes forming an image of a region of interest from the x-rays transmitted through the region of interest. The method further includes combining the images to form an unobstructed view of the corresponding regions of interest.

BRIEF DESCRIPTION OF THE DRAWINGS

FIG. 7 is a perspective view of a first plane shown in FIGS. 5 and 6;

FIG. 8 illustrates two solutions in accordance with the present invention for imaging below the horizontal row of obscuring objects shown in FIG. 7.

DETAILED DESCRIPTION OF AN EMBODIMENT OF THE INVENTION

Figure 1A:
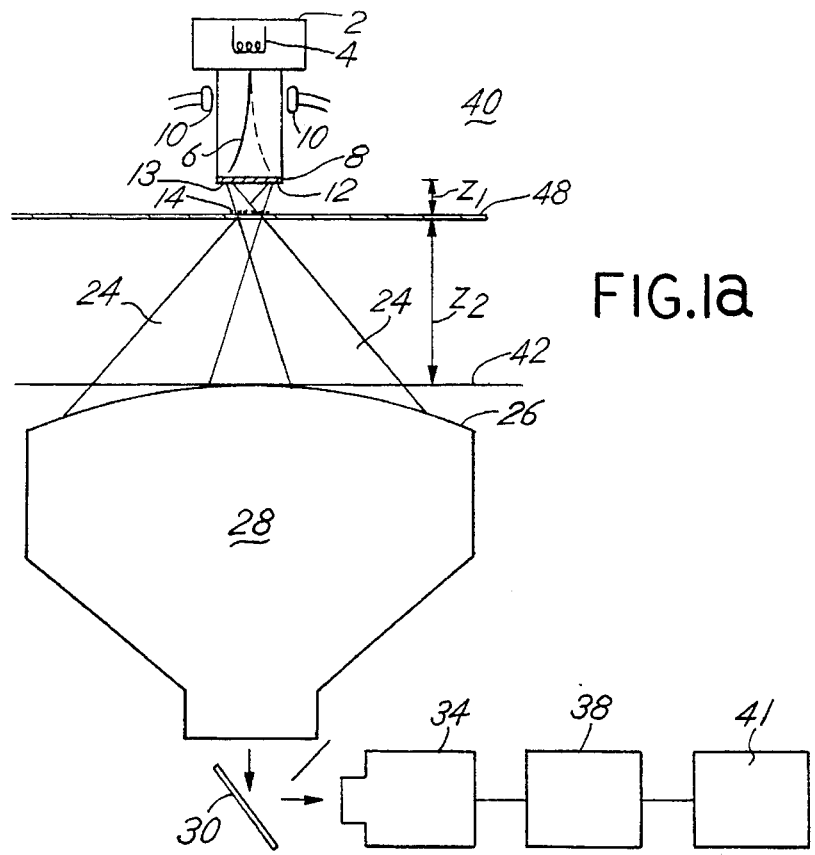
FIG. 1a is a schematic diagram of an embodiment of an x-ray imaging system to be used in conjunction with the present invention.

The present invention is best understood upon viewing the embodiments illustrated in FIGS. 1–9, where like elements are denoted by like numerals. FIGS. 1a–d each show an x-ray source 2 that preferably incorporates a cathode 4 for producing an electron beam 6. The electron beam 6 is directed toward a grounded transmission anode target 8 that preferably is made of tungsten. It is understood that other configurations for the x-ray source 2 are possible without falling outside the spirit of the invention, such as having anode 8 be a reflection-type target.

The cathode 4 is supplied with a current of approximately 0.1 ma and may have a voltage ranging from −60 kV to −160 kV with respect to the target anode 8. Preferably, the cathode voltage is computer controlled so that during an inspection cycle the voltage may be optimally adjusted for imaging the region of interest. Generally, the optimum cathode voltage increases with increasing opacity of a test object 14. At the optimum cathode voltage, which is typically between −60 kV and −125 kV for a PCB, the x-ray source 2 produces an x-ray beam 24 having sufficient energy to penetrate the test object 14 and also having low enough energy so that a resulting image has contrast within the region of interest.

The x-ray source 2 preferably is a microfocus x-ray source in which the electron beam 6 emitted from the cathode 4 is deflected to strike discrete and predetermined focal spot locations 36 on the anode target 8. Deflection of the electron beam 6 during operation may be accomplished by magnetic coils 10 under local computer control. An example of such an x-ray source 2 is described in U.S. Pat. No. 5,020,086 the contents of which are incorporated herein by reference. Alternatively, the electron beam 6 may be deflected electrostatically.

The x-rays emitted from anode 8 pass through a window 12 made of an x-ray transparent material such as Beryllium and/or through an x-ray spectrum filter 13. The x-ray spectrum filter 13 may be chosen to modify the x-ray energy spectrum in such a way that adjusts the sensitivity of the system to the component under inspection. In addition, an electrically actuated mechanical shutter (not shown) may be provided to contain the emitted x-rays without interrupting power to the x-ray source 2. Note that the shutter may be moved pneumatically in response to an electrical signal from a solenoid.

Figure 1B:
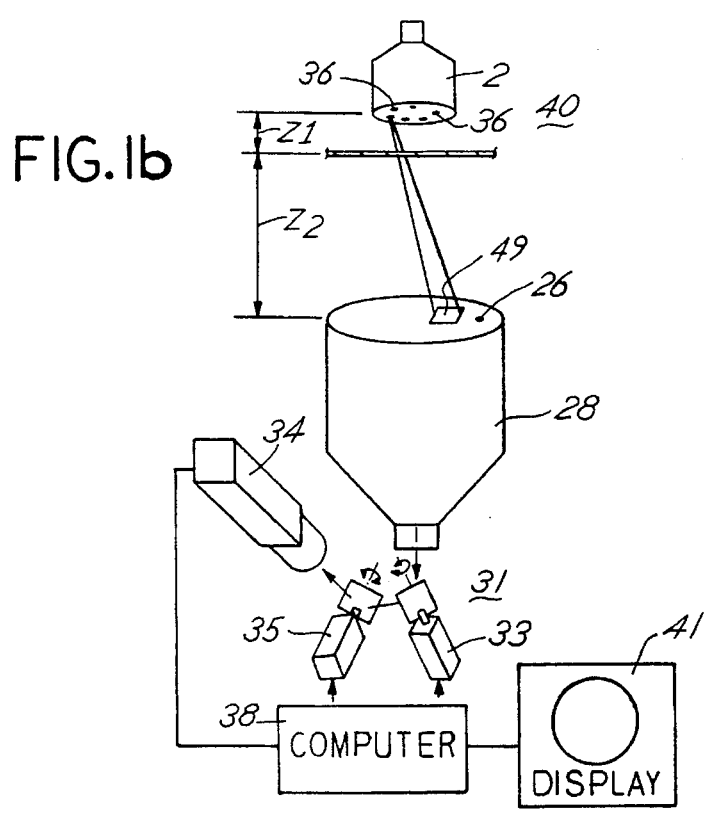
FIG. 1b is a schematic diagram of a second embodiment of an x-ray imaging system to be used in conjunction with the present invention.
Figure 1D:
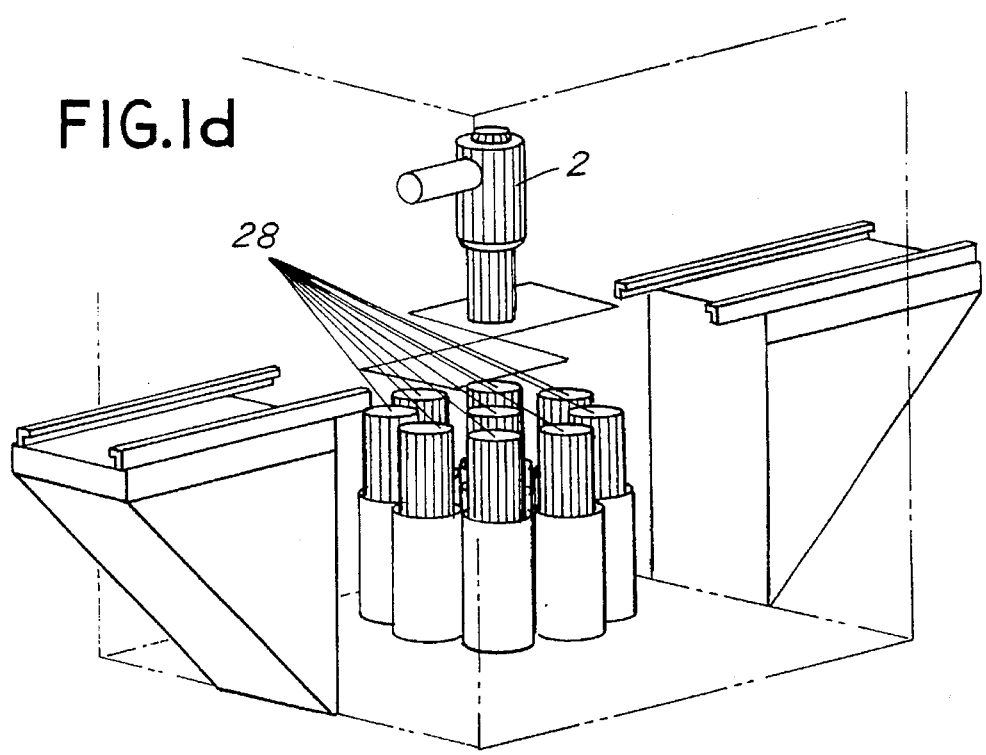
FIG. 1d illustrates an arrangement of image intensifiers for use in the x-ray imaging system shown in FIG. 1c.
Figure 1C:
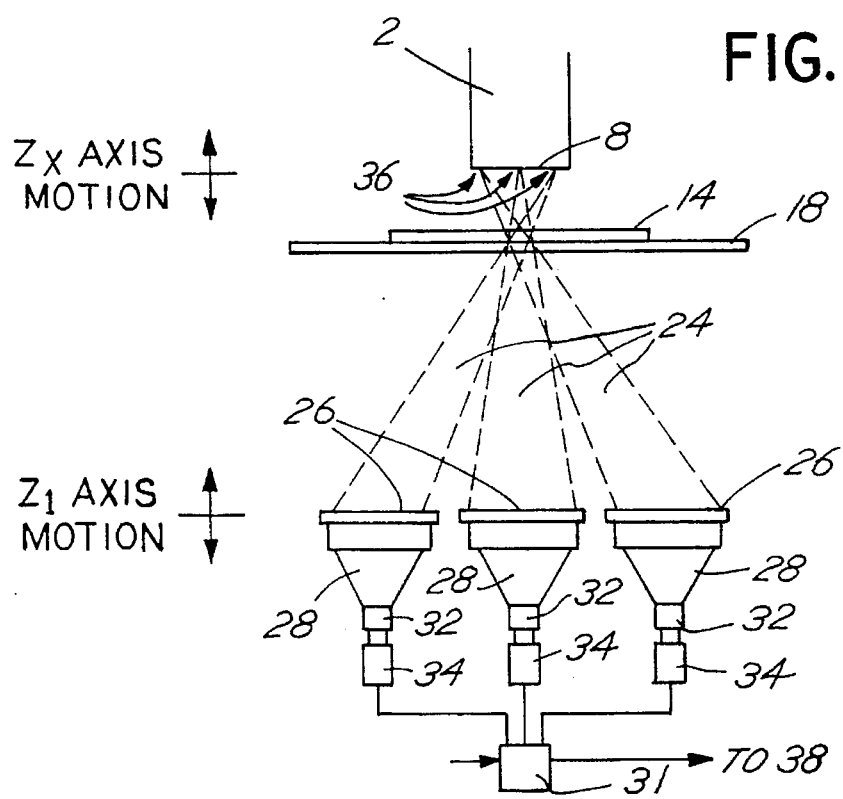
FIG. 1c is a schematic diagram of a third embodiment of an x-ray imaging system in accordance with the present invention.

As shown in FIGS. 1a, 1b and 1c, the x-rays generated by source 2 are directed toward the test object 14. Though the choice of the test object 14 is arbitrary, for the present invention the test object 14 preferably comprises either an electronic assembly or a circuit board including electronic components electrically connected to the circuit board through solder joints. The present invention allows one to identify defects in circuit boards as disclosed in U.S. Pat. No. 4,809,308, whose entire contents are incorporated herein by reference.

Figure 2:
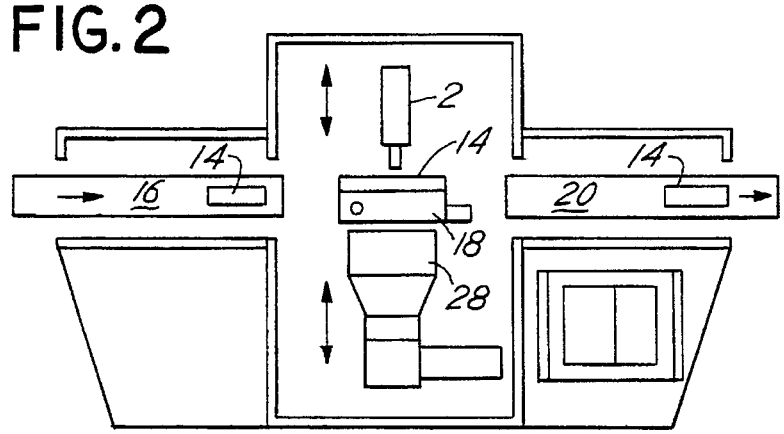
FIG. 2 is a cross-sectional view of an object handling device to be used in conjunction with the x-ray imaging systems of FIGS. 1a–b.

A handling system may be provided to automatically load test objects to, and unload test objects from, the x-ray imaging systems shown in FIGS. 1a through 1c. As schematically shown in FIG. 2, an inlet conveyor 16 transports the test object 14 from an outside factory conveyor to an X-Y table 18. Once the X-Y table 18 has received the test object 14, the x-ray imaging inspection cycle can begin while the outlet conveyor 20 returns the previously inspected test object to the factory and the inlet conveyor 16 retrieves the next test object. The handling system is further described in pending U.S. patent application Ser. No. 08/299,928.

When the test object 14 is mounted on the X-Y table 18, the test object 14 may be translationally moved along the x and y directions so that an area of interest, such as a solder joint, can be imaged. Once the test object 14 is properly positioned, a beam of radiation, such as the x-ray beam 24, is projected towards the solder joint on the test object 14. The x-ray beam 24 originates from the appropriate predetermined location 36 on the target 8 of the x-ray source 2. A portion of the x-ray beam 24 is transmitted through and modulated by the test object 14, after which the x-ray beam 24 strikes a detector that is capable of producing an x-ray shadowgraph containing the modulation information from the test object. An example of such a detector is a fluorescent or scintillating screen 26 supported by an image intensifier 28. As shown in FIG. 1a, the image intensifier 28 is positioned in-line with the x-ray beam 24.

The x-rays striking the fluorescent or scintillating screen 26 produce a visible light or shadowgraph image of the volume of the object 14 that falls within the x-ray beam 24. If the detector includes an image intensifier 28, as shown in FIGS. 1a through 1d, the image at the output of the image intensifier is amplified in brightness.

The image intensifier 28 in the embodiments of FIGS. 1a–d and 3 is positioned to receive the x-rays that are transmitted through the test object 14. The face plate of the image intensifier 28 is preferably formed by the fluorescent or scintillating screen 26, which converts x-rays to visible light. The screen 26, which is typically curved or spherically shaped, captures individual images that are viewed by a camera 34, such as a CCD camera, and subsequently digitized by the image processor 38. The use of an image intensifier in the imaging chain has the distinct advantage of high conversion efficiency resulting in improved signal-to-noise ratio over passive screen-based conversion systems. This feature permits optimizing the field-of-view, resolution, and throughput for virtually any board type, even if the board has a wide variation of component pitch.

The use of a large format imaging system, such as the image intensifier 28, shown in FIGS. 1a–b, eliminates the need to have a spinning detector, reducing the mechanical complexity of the system and improving system reliability and the repeatability of results. This approach simplifies the mechanical requirements for the image collection system and allows static rather than dynamic image train alignment and calibration. Distortion in the visible light images that may be produced when the images are projected toward the outer circumference of the curved or spherical screen 26 on the image intensifier 28 may be corrected as described in pending U.S. patent application Ser. No. 08/224,629, whose entire contents are incorporated herein by reference.

The x-ray source 2 and the image intensifier 28 are mounted on independent vertical drive mechanisms allowing a continuously variable field-of-view, ranging from approximately 0.1" to approximately 1.0", to be obtained. In particular, the x-ray source 2 is mounted on a programmable Z-axis, which changes the distance between the target anode 8 and a plane 48 containing the region of interest within or on the surface of the test object 14. The distance between the x-ray source 2 and the plane 48 is referred to herein as $Z_1$. The image intensifier 28 is also mounted on a programmable Z-axis, which changes the distance between the object plane 48 and the screen 26. The distance between the plane 48 and the screen 26 is referred to herein as $Z_2$. Variation of the field of view may be accomplished by varying either or both of the distances $Z_1$ and $Z_2$. The imaging system described herein may be calibrated along the Z-axis as disclosed in pending U.S. patent application Ser. No. 08/224,634 to provide an improved representation of the region of interest.

The visible light image produced by the screen 26 and the image intensifier 28 may be reflected by an optical system. In FIG. 1b, a preferred optical system is shown. The optical system includes a computer-controlled view selector 31, which improves the resolution of the system. During image collection, the view selector 31 is synchronized with the movement of the x-ray focal spot to the predetermined locations 36 to provide a selected portion of the visible light image from the screen 26 of the image intensifier 28 to the camera 34. The camera 34 typically is capable of providing a 512×512 pixel video image. Because the view selector 31 provides only the selected portion of the entire image intensifier surface to the camera 34, the resolution of the imaging system is increased.

As shown in FIG. 1b, the view selector 31 preferably contains two independently rotatable mirrors 33 and 35, the first mirror 33 being rotatable so as to vary the location of the selected portion of the image intensifier surface along the X-axis. The second mirror 35 is rotatable so as to vary the location of the selected portion of the surface along the y-axis. The mirrors 33 and 35 may be controlled by a computer 38 so that the image reflected from the mirrors is received by camera 34, in which case the computer 38 may also control the deflection of the electron beam 6 in synchronization with the movement of the mirrors 33 and 35 and the cathode voltage.

Alternatively, the optical system may be a planar mirror 30 having an aluminized front surface, as shown in FIG. 1a. The mirror 30 may be mounted at an angle of 45 degrees to the horizontal to reflect the visible light image from the image intensifier 28 through 90 degrees. The visible light image is amplified in brightness by the image intensifier 28 and is then reflected at a 90 degree angle by the mirror 30 to a lens 32 mounted upon a video camera 34. The mirror 30 allows the camera 34 to be positioned outside the path of the x-ray beam 24 when a non-x-ray-opaque detector is used or to conserve vertical space. The mirror 30 is not required if the detector is opaque to x-rays or if the camera 34 is not sensitive to x-rays.

In an alternative embodiment, the large format image intensifier 28 is replaced by multiple small-format image intensifiers. In FIGS. 1c–d, an arrangement of nine small-format image intensifiers is illustrated. A camera 34 may be used for each of the multiple small-format image intensifiers, in which case the view selector 31 including the rotating mirrors 33 and 35 is unnecessary.

Like the large format image intensifier 28, the arrangement of small-format image intensifiers eliminates the need to have a spinning detector and allows static rather than dynamic image train alignment and calibration. A benefit provided by the small-format image intensifiers is that, because the curved or spherical screen 26 is much smaller, the small-format image intensifier produces less distortion when a visible light image is projected toward its outer circumference. However, the arrangement of small-format image intensifiers may limit the selection of the predetermined locations 36.

A single camera 34 in conjunction with a view selector, such as the view selector 31, and a bundle of fiber optic cables may alternatively be used with the arrangement of small-format image intensifiers. For each of the small-format image intensifiers, a fiber optic cable may couple the visible light image from the image intensifier to the view selector 31.

A commercially available CCD camera that is suitable for these applications is available from Cohu, Inc. of San Diego, Calif. as Model No. 4915. It is envisioned that, as CCD camera technology develops, a CCD camera that is capable of providing approximately 3000×3000 pixel resolution will become available. If such a CCD camera were used with the large format image intensifier 28 the view selector 31 would no longer be required, as the CCD camera would be capable of viewing the entire screen 26 on the image intensifier 28 while providing equivalent resolution to the currently available 512×512 pixel CCD cameras. In the same manner, a single 3000×3000 pixel CCD camera could be used to view the multiple small-format image intensifiers by using fiber optic cables to transmit the visible light images from the small-format image intensifiers to the CCD camera.

The analog output of CCD camera 34 is provided to image processing/defect recognition system 38 which processes the image information to formulate an image on a display, such as a video monitor 41, or to provide a printed defect analysis, as described in U.S. Pat. No. 4,809,308. The image processing/defect recognition system may also provide feedback for process control.

Another function performed by image processing system 38 is to calibrate the imaging system prior to imaging a region of interest, such as a solder joint. In particular, an angular calibration system 40 accurately determines the angular direction θ of the x-ray beam 24. The preferred angular calibration system is disclosed in pending U.S. patent application Ser. No. 08/224,634, which is entitled "X-ray Position Measuring and Calibration Device" and whose entire contents are expressly incorporated herein by reference. It is to be understood that other calibration systems may be used without departing from the spirit of the present invention, as long as the angle θ may be accurately determined.

Figure 3:
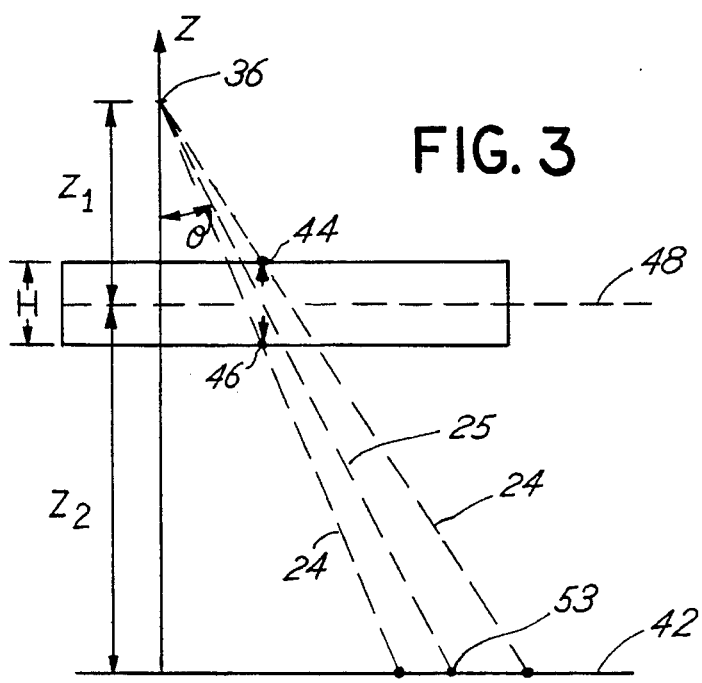
FIG. 3 is a schematic diagram of an embodiment of an angular calibration system according to the present invention.
Figure 4:
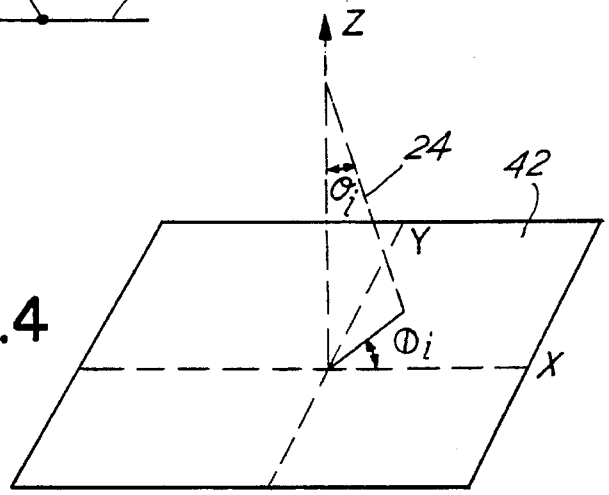
FIG. 4 is a diagram defining the angular values of an x-ray beam emitted from the x-ray imaging systems of FIGS. 1a–d.

The angular calibration system 40 utilizes the x-ray imaging system described previously and shown in FIGS. 1a–d to accurately determine the angle θ. FIG. 3 illustrates a portion of the calibration system 40 in greater detail. A radiation source, such as the x-ray source 2, is located along a first direction, such as the Z-axis. As described in U.S. patent application Ser. No. 08/224,634, the radiation source 2 generates a beam of radiation, such as x-ray beam 24, where the beam axis 25 is directed along an inclinational angular direction given by θ and φ measured with respect to the Z-axis. Furthermore, when viewed along the Z-axis, the beam axis 25 of the x-ray beam 24 strikes an image plane 42 at an azimuthal angle φ with respect to the X-axis, as shown in FIG. 4. It should be noted for purposes of the present invention that the inclinational angular direction θ may also be represented by the components $\theta_x$ and $\theta_y$, rather than the angles θ and φ, by transforming the angles θ and φ from polar to cartesian coordinates. The angles θ and φ, and any components thereof, are measured with respect to the beam axis 25, as shown in FIGS. 3 and 4.

The angular calibration system 40, as described in pending U.S. patent application Ser. No. 08/224,634, allows the inclinational angular direction θ to be accurately determined for an x-ray beam generated from any predetermined location 36 of the electron beam focal spot on the target anode 8. During a board inspection cycle, images are projected toward specific locations on the surface 26 of the image intensifier 28 by moving the electron beam 6 to a set of predetermined focal spot locations 36 on target anode 8. Once the electron beam 6 strikes the anode 8 at one of the predetermined focal spot locations 36, an x-ray beam 24 is emitted toward the object 14. For a given predetermined location 36, the emitted x-ray beam 24 will be directed toward the object 14 at a given inclinational angular direction θ, which, as described above, may be described by its orthogonal components $\theta_x$ and $\theta_y$. Accordingly, a source image 49 will be formed at the screen 26 for each of the predetermined locations 36.

As discussed above, U.S. Pat. No. 5,097,492 shows an electron beam within an x-ray source is deflected to scan a continuous circular pattern on a target anode. The detector also rotates in a circular pattern. U.S. Pat. No. 5,020,086 describes an imaging system in which a series of images are obtained by scanning an electron beam stepwise through a circular pattern about a central axis. The series of images are then combined to form a representation of a region of interest. Without knowledge of the geometry of the body or bodies obscuring the region of interest, the circular scanning pattern may be assumed to provide an acceptable representation of the region of interest. In accordance with the present invention, however, information about the geometry of the obscuring body or bodies may be used to provide an improved representation of the region of interest.

In accordance with the present invention, the imaging geometry used to produce the representation of the two-dimensional plane may be optimized for a particular test object to reduce the data required to produce the two-dimensional representation and to minimize the effects in the representation of substances located above or below the desired two-dimensional plane. The imaging geometry, as used herein, refers to the pattern of the predetermined locations 36 on the target anode 8, and the corresponding inclinational angular direction θ of the resulting x-ray beam 24.

Figure 5:
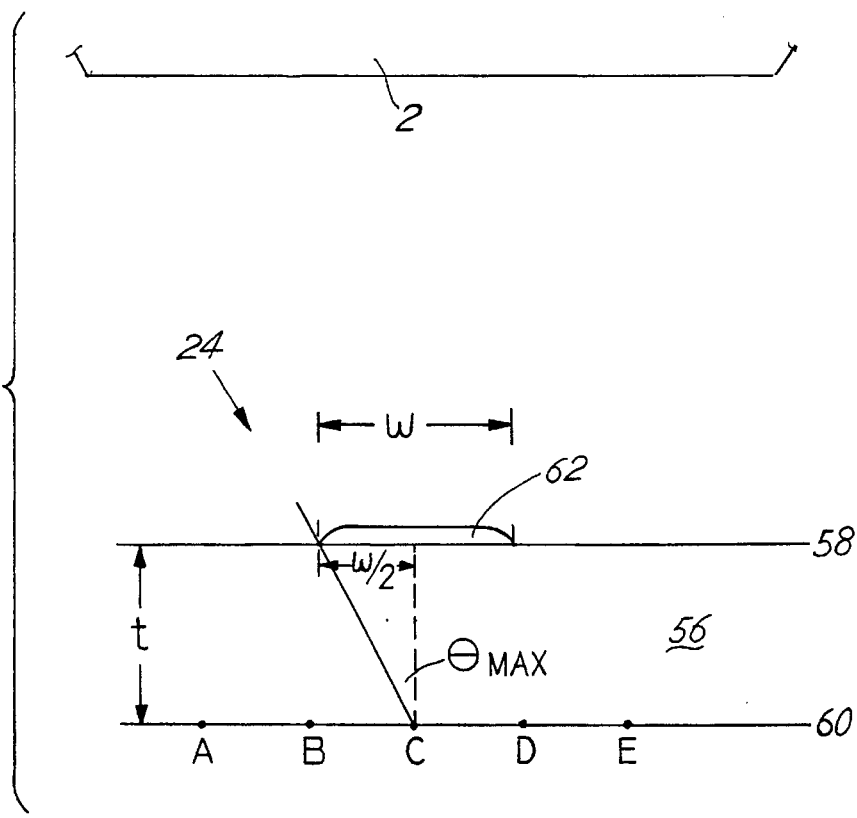
FIG. 5 is an illustration of a portion of a test object having an obscuring body, in which the illustration defines dimensions that may be used in selecting angular values as defined in FIG. 4.

Referring now to FIG. 5, a portion of a test object 56 is shown. The test object includes a first plane 58 and a second plane 60. The first plane 58 is positioned nearer to the x-ray source 2 than is the second plane 60, and the first plane 58 is separated from the second plane 60 by a distance t. The distance t is measured along the Z-axis with the intersection of the Z-axis with the plane 60 defining the origin. Accordingly, if the second plane 60 was located above the first plane 58, then the value of t would be negative. An x-ray opaque body 62 having a width w is located about the first plane 58. In the example of FIG. 5, the second plane 60 defines the region of interest within the test object 56.

Although the body is described as being opaque, it is to be understood that it is not necessary that the body completely block the transmission of x-rays. Rather, as used herein, an opaque body is a body that attenuates x-rays to a greater extent than the material surrounding the body. The three-dimensional construction of a PCB-mounted solder connection is nearly binary in x-ray attenuation characteristics. Each volume element (voxel) can be modeled as being entirely filled with either metal (i.e., solder or metal wire), or a low x-ray attenuation material (i.e., air, plastic, organic material, etc.).

In order to obtain an unobstructed representation of the second plane 60, the electron beam 6 within the x-ray source 2 must be deflected to more than one predetermined location 36, creating corresponding source images for each predetermined location. There will be a minimum number of predetermined locations 36 that are required so that every part of the region of interest, in this example the second plane 60, may be imaged without obstruction by the body 62 in at least one of the source images.

Referring again to FIG. 5, a point C is illustrated in the second plane 60. The point C is located within the second plane 60 at the distance t below the midpoint w/2 of the body 62. To obtain an unobstructed image of the point C, the x-ray beam 24 must be generated frown an appropriate predetermined location 36 such that the x-ray beam 24 passes beside rather than through the body 62. As shown in FIG. 5, the maximum angle of x-ray beam inclination that satisfies this requirement is:

$$\theta_{max}=\arctan(w/2t)$$

An unobstructed image of points A and B within the second plane 60 may be obtained frown inclination angles of $\theta_{max}$ or less, while an unobstructed image of points D and E may be obtained from inclination angles between 0 and $-\theta_{max}$. Accordingly, the smallest range of inclination angle values that may be used to obtain an unobstructed representation of the second plane 60 is given by:

$$-\theta_{max} \leq \theta \leq \theta_{max}$$

Generally, it is preferable to utilize the minimum number of images that will provide an unobstructed view of the region of interest. An unobstructed representation of the second plane 60, including points A through E, may be obtained from two images, a first image obtained at the inclination angle of $-\theta$ and a second image obtained at the inclination angle of $\theta$. As may be seen from FIG. 5, $+\theta$ and $-\theta$ are the minimum angles of inclination for an unobstructed representation of the second plane 60. Larger angles may alternatively be used and it is not necessary that the + and − angles be of the same magnitude.

Figure 6:
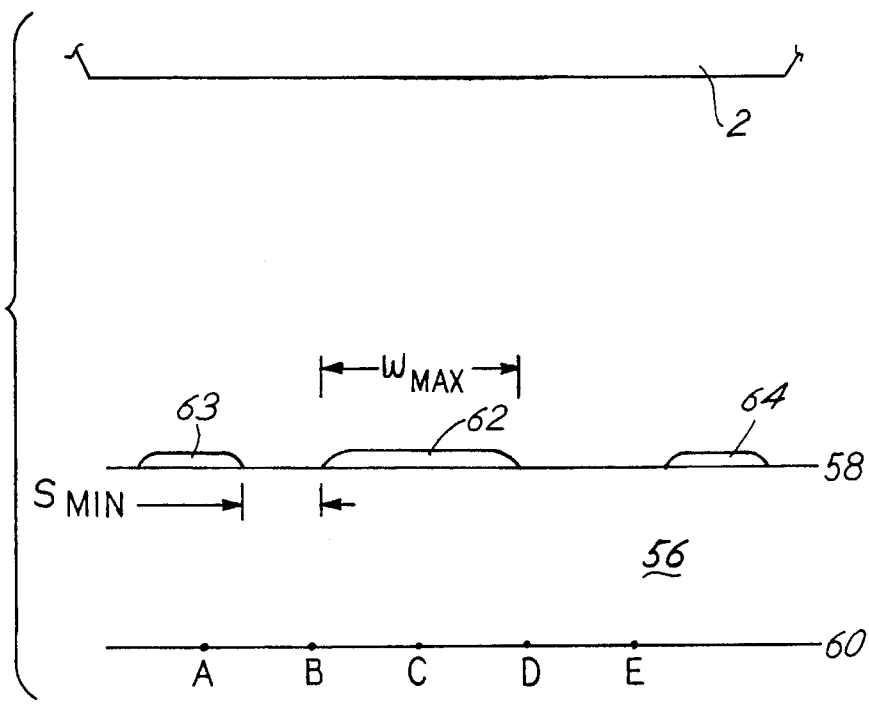
FIG. 6 is an illustration of a portion of a test object for further defining dimensions that may be used in selecting angular values in accordance with the present invention.

FIG. 6 is a cross-sectional view of a test object, which is like the test object shown in FIG. 5 except that additional bodies, such as the bodies 63 and 64 are disposed about the first plane 58. The minimum separation between any two adjacent bodies is the distance $s_{min}$. For purposes of the following analysis, it is assumed that the distance $s_{min}$ and w are small with respect to $Z_1$. An unobscured representation of the second plane 60 may be obtained by using the separation of distance $s_{min}$ between adjacent bodies as a "window" to the region of interest. In accordance with the present invention, the inclination angle may be incremented to "walk" the view within the window across the region of interest.

The movement of each view through a given window resulting from a change in angle $\Delta\theta$ will be t×tan($\Delta\theta$), for small angles θ. In order that the views overlap, it is necessary that t×tan($\Delta\theta$)$\leq s_{min}$, which therefore limits the angular increment $\Delta\theta$ to $\Delta\theta \leq \arctan(s_{min}/t)$.

In the example described with respect to FIG. 5, it was shown that two images obtained by angles of inclination separated by $2\theta_{max}$ provided an unobscured representation of the region of interest, i.e., the second plane 60. Where the test object includes an arrangement of bodies, as shown in FIG. 6, an unobscured representation of the region of interest may be obtained from a series of images in which the inclination angle is incremented by $\Delta\theta$ across the range of $2\theta_{max}$.

For an arrangement of bodies as shown in FIG. 6, $\theta_{max}$ as given by equation 1 is calculated from the maximum width $w_{max}$ associated with the bodies. In the case of the bodies being periodically disposed about the plane 58, the dimensions s and w will be constants. The body 62 in FIG. 6 has the maximum width. The total number of images required is:

$$n=[2\theta_{max}/\Delta\theta]$$

which is preferably rounded up to the next integer. Preferably, the overlap of the views of the second plane 60 are evenly distributed by using the integer value n to recalculate the incremental angle, $\Delta\theta$ as follows:

$$\Delta\theta=2\theta_{max}/n_{integer}$$

The above discussion assumes that a given $\Delta\theta$ will produce a given movement of the unobscured view across the second plane 60. This assumption is only true for small values of θ. An alternative approach that is not constrained to small values of θ is to allow the position of the view to move in evenly sized steps across the second plane 60 and to compute the angle θ corresponding to each such position.

If the variable view position is measured in respect to the view position when θ=0, then the view must take positions from −w/2 to +w/2. The number of steps will be n=w/s$_{min}$, which is rounded to the next highest integer. The positions of the view will therefore be:

$$Pi = -\frac{w}{2} + i\frac{w}{n},$$

where i varies from 1 to n. The corresponding angles θ$_i$ are:

$$\theta_i = \tan^{-1}\left(\frac{Pi}{t}\right).$$

This general formulation will produce an efficient set of inclinational angular directions for all obscuring geometries. However, in some cases, an equivalent quality representation of the plane 60 may be produced from a smaller set of inclinational angular directions, depending on the particular geometry of the obscuring bodies on or within the test object.

If the obscuring bodies have a vertical dimension h that is significant in comparison to the separation s between the bodies, then the above calculations must be modified to account for the corresponding effective reduction in size of the separation s. At a given angle θ, s$_{effective}$=s−h tan(θ). In this case, the above θ$_i$ calculation may be repeated with the steps made smaller to account for the smaller s$_{effective}$ as a function of the angle θ.

The predetermined locations 36 of the electron beam focal spot on the target anode 8 for imaging the test objects in FIGS. 5 and 6 lie along a line that is parallel to the bottom of the page on which the figure is shown. Some test objects may, however, present a more advantageous imaging geometry in another direction. For example, a test object as shown in FIG. 6 may have the bodies arranged in another direction in which the width w of the bodies is smaller and/or the separation s between the bodies is greater in another direction. In this case, it is preferable to direct the focal spot to predetermined locations 36 along a line in that direction because fewer images are required to provide an unobstructed view of the region of interest.

In an alternative arrangement of the test object, different features may be analyzed along differing directions, producing differing sets of the required θ components in each direction. The region of interest may then be represented for a given obscuring geometry by using a set of θ and φ values that includes all of the required θ components.

For example, one specific case of an obscuring geometry is given by the horizontal row of obscuring objects 70 in FIG. 7. Since the obscuring objects 70 are thinner (smaller w) in the horizontal direction, the analysis should be performed in that direction, producing required angular components in that direction (θ$_x$). From the above analysis, $$\theta_x = \tan^{-1}\left(\frac{W_x}{2t}\right) \text{ and } \Delta\theta_x \leq \tan^{-1}\left(\frac{S_x}{t}\right).$$

The above analysis does not specify the y-component of the angles. These can be chosen on any convenient basis. Obvious choices are θ$_y$=0, resulting in a linear "scan," or setting θ$_y$ to the maximum available angle. This latter choice is especially useful if more than the minimum number of viewing angles are to be used. In this case, θ$_y$ can take values of plus and minus the maximum available angle, thus providing flexibility to account for obscuring features not accounted for in the basic analysis (e.g., lead frames, ground planes, etc.).

FIG. 8 shows these possible options for imaging the horizontal row. In this plot, points are plotted in x and y according to their θ$_x$ and θ$_y$ components. The plotted points represent the selected predetermined locations 36 on the target anode 8. The plotted points, "x", represent the linear scan solution, i.e., θ$_y$=0. The plotted points, "●", represent the solution in which θ$_y$ is set to + and − the maximum available angle. The predetermined locations 36 represented by θ$_x$ and θ$_y$ may alternatively be represented in terms of the θ and φ values described above by the equations:

$$\theta = \sqrt{\theta_x^2 + \theta_y^2} \text{ and } \phi = \tan^{-1}\left(\frac{\theta_y}{\theta_x}\right),$$

which describe the usual cartesian-to-polar coordinate transformation.

The analysis can be expanded to include the vertical row of features in FIG. 7. FIG. 7 is a perspective view of the plane 58 taken along the Z-axis, i.e., the plane 58 lies in the x-y plane. For these features, the analysis is best done in terms of θ$_y$, since their vertical dimension is smaller. Combining this analysis for θ$_y$ with the θ$_x$ results above places conditions on both θ$_x$ and θ$_y$:

$$\theta_{x \, max} = \tan^{-1}\left(\frac{W_x}{2t}\right), \Delta\theta_x \leq \tan^{-1}\left(\frac{S_x}{t}\right)$$

$$\theta_{y \, max} = \tan^{-1}\left(\frac{W_y}{2t}\right), \Delta\theta_x \leq \tan^{-1}\left(\frac{S_y}{t}\right).$$

Figure 9:
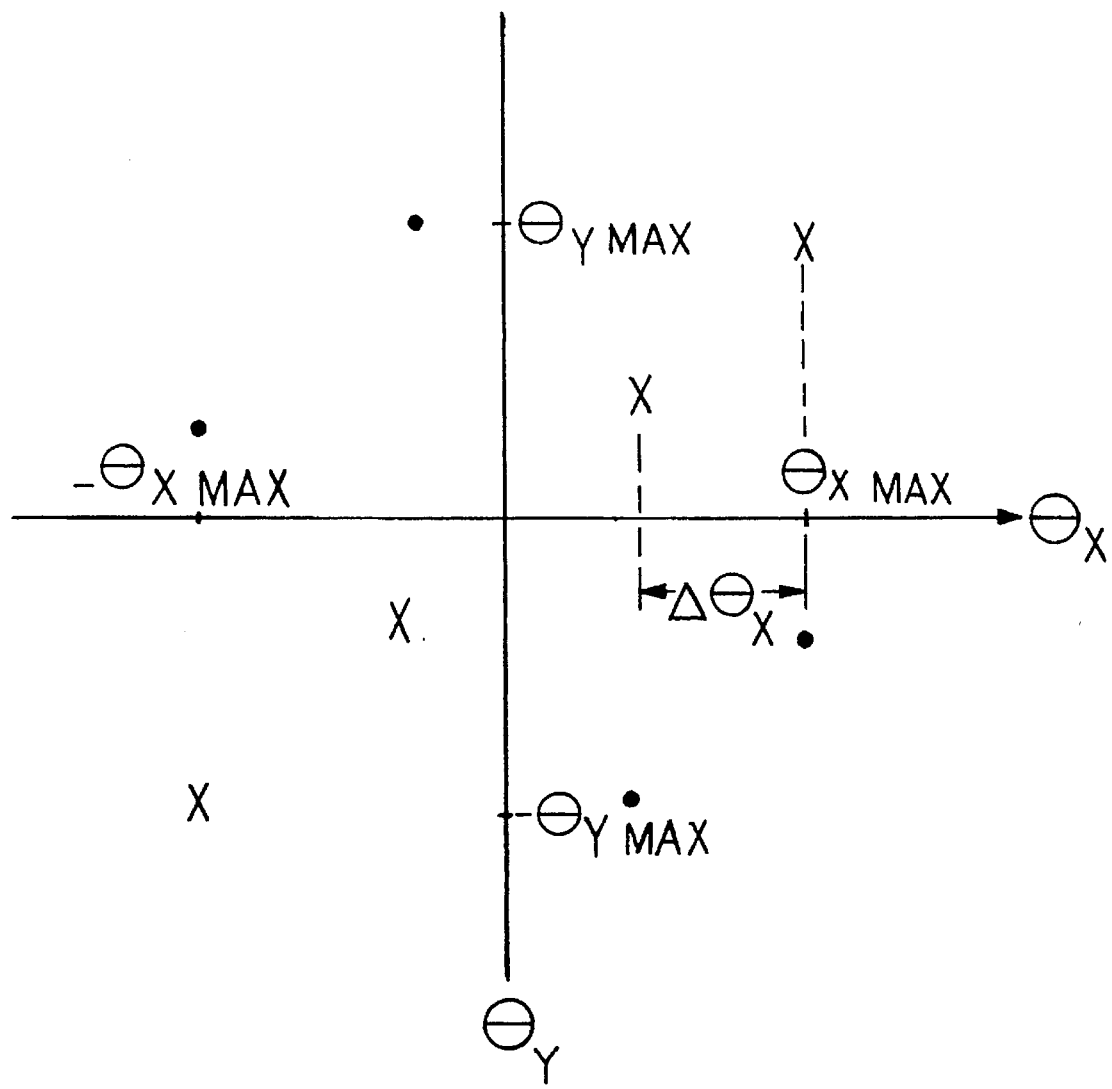
FIG. 9 illustrates the solutions in accordance with the present invention for imaging below the horizontal and vertical rows of obscuring objects shown in FIG. 7.

FIG. 9 shows two of the many options for meeting these conditions. A first solution is represented by the plotted points, "x", and a second solution is represented by the plotted points, "●".

Although the obscuring objects shown in FIGS. 5–7 are arranged about a plane located above the plane containing the region of interest, it is to be understood that the present invention is not limited to this arrangement. The region of interest may lie on the surface of the test object or in any plane within the test object. For example, when the plane 60 containing the region of interest is located above the plane 58 containing the obscuring bodies, the value of the distance t will be negative in the above equations. Therefore, for any location of the region of interest, the present invention provides predetermined locations 36 for obtaining an unobscured representation of the region of interest.

Accordingly, by using an imaging geometry that is not constrained to a circular pattern, an improved representation of a region of interest may be obtained. In the instance where the test object 14 is a PCB, the flexibility of defining the pattern of predetermined locations 36 on the target anode 8 according to the geometry of the obscuring body or bodies improves the quality of the representation of the region of interest, while decreasing inspection times. On a PCB, surface mounted devices frequently obscure the regions above or below the devices. Many of these devices have a square or rectangular geometry so that the regions above or below these devices are best represented by using a non-circular scanning geometry, as described above. In addition, many of these devices have a periodic arrangement of leads that may obscure regions above or below the device. Of course, where the device geometry is circularly symmetric, such as where the devices are ball grid arrays or flip-chip attach arrays, the present invention may utilize a circular scan geometry to obtain the best representation of a region below the devices. It should be noted that, as PCB device geometries change with future developments, the present invention provides a means to select the optimum imaging geometry. Moreover, it is to be understood that the above-described determination of the optimum imaging geometry may be applied to test objects other than PCBs.

In accordance with the present invention, apparatus is, therefore, provided for producing an unobscured representation of a region of interest. In addition, the present invention provides a method of selecting the predetermined locations 36 in order to efficiently and effectively produce an unobscured representation of the region of interest.

It is envisioned that the present invention may be used in conjunction with the apparatus and method for forming a reconstructed image as described in pending U.S. patent application Ser. No. 08/224,629. As described in Ser. No. 08/224,629, rather than simply summing eight corresponding pixels from eight source images to form a single pixel in the reconstructed image, the invention described in Ser. No. 08/224,629 combines the pixels in a non-linear manner. The present invention may be utilized to provide unobscured source images, which may result in an improved reconstructed image.

While the invention has been described with relation to certain presently preferred embodiments, it is understood that the invention as expressed in the claims is not limited to those described preferred embodiments. Those with skill in this art will recognize other modifications of the invention which will still fall within the scope of the invention, as expressed in the accompanying claims.

We claim:

1. An apparatus for imaging a region of interest that is positioned on or within a test object that is obscured by a first obscuration body positioned on or within said test object but positioned outside said region of interest, comprising:

an x-ray source having a cathode for producing a steerable electron beam;

a controller coupled to the x-ray source, wherein the controller directs the electron beam to predetermined locations on a target anode, the predetermined locations being determined from an obscuration geometry of the first body relative to the area of interest;

a detector positioned to receive x-rays that are transmitted through the test object from each of the predetermined locations and to produce images corresponding to each of the predetermined locations; and an imaging system that combines the images to produce an unobscured image of said region of interest.

2. The apparatus of claim 1, wherein said area of interest lies within a plane.

3. The apparatus of claim 1, wherein said object is positioned nearer to said x-ray source than said area of interest.

4. The apparatus of claim 1, wherein said item of interest is a circuit board.

5. The apparatus of claim 4, wherein said object is solder.

6. A method of imaging a region of interest that is positioned on or within a test object that is obscured by a first obscuration body positioned on or within said test object but positioned outside said region of interest, comprising:

generating an electron beam;

directing the electron beam to predetermined locations on a target anode, wherein the predetermined locations are selected from a set of locations on the target anode determined from an obscuration geometry of the first body relative to the area of interest, whereby an x-ray beam is emitted toward the test object from the predetermined locations on the target anode; and for each of the predetermined locations, forming an image of said region of interest on or within the test object by detecting a portion of the x-ray beam transmitted through the region of interest.

7. A method as claimed in claim 6, wherein the predetermined locations are determined from an obscuration geometry of the first body and a second obscuration body relative to the area of interest.

8. The method of claim 6, wherein said area of interest lies within a plane.

9. The method of claim 6, wherein said object is positioned nearer to said x-ray source than said area of interest.

10. The method of claim 6, wherein said object is separated from said area of interest by a distance t as measured along an axis;

said body having a width w; and wherein said x-ray beam forms a beam of inclination that is greater than or equal to:

$$\theta_{max} = \arctan(w/2t).$$

11. The method of claim 10, wherein said area of interest is entirely imaged only by x-ray beams that have an angle of inclination $\theta$ according to the relationship:

$$-\theta_{max} \leq \theta \leq \theta_{max}.$$

12. The method of claim 10, wherein the angles of inclination that entirely image said area of interest are subtended by an angular range $2\theta_{max}$.

13. The method of claim 12, wherein adjacent locations produce x-ray beams that consecutive x-ray beams are angularly stepped relative to one another and the angular separation between consecutive x-ray beams differs by no more than $\Delta\theta = 2\theta_{max}/n_{integer}$, where $n_{integer}$ is equal to the total number of locations.

14. The method of claim 6, comprising a second object, wherein said first and second objects are separated from said area of interest by a distance t as measured along an axis;

said second body having a width w that is greater than or equal to the width of said first object; and wherein said x-ray beam forms a beam of inclination that is greater than or equal to:

$$\theta_{max} = \arctan(w/2t).$$

15. The method of claim 14, wherein said area of interest is entirely imaged only by x-ray beams that have an angle of inclination $\theta$ according to the relationship:

$$-\theta_{max} \leq \theta \leq \theta_{max}.$$

16. The method of claim 14, wherein the angles of inclination that entirely image said area of interest are subtended by an angular range $2\theta_{max}$.

17. The method of claim 16, wherein adjacent locations produce x-ray beams that consecutive x-ray beams are angularly stepped relative to one another and the angular separation between consecutive x-ray beams differs by no more than $\Delta\theta = 2\theta_{max}/n_{integer}$, where $n_{integer}$ is equal to the total number of locations.

18. The method of claim 6, comprising a second object and a third object, wherein said first, second and third objects are separated from said area of interest by a distance t as measured along an axis;

said first and second objects are separated from one another by a distance $s_{min}$ that is smaller than both the distance separating the second and third objects and the distance separating the first and third objects;

wherein the greatest width of said first, second and third bodies is denoted by w; and wherein said x-ray beam forms an angle of inclination that is greater than or equal to:

$$\theta_{max}=\arctan(w/2t).$$

19. The method of claim 18, wherein said area of interest is entirely imaged only by x-ray beams that have an angle of inclination θ according to the relationship:

$$-\theta_{max} \leq \theta \leq \theta_{max}.$$

20. The method of claim 18, wherein the angles of inclination that entirely image said area of interest are subtended by an angular range 2θmax.

21. The method of claim 20, wherein adjacent locations produce x-ray beams that are angularly separated from one another by no more than $\arctan(s_{min}/t)$.

22. The method of claim 6, comprising a second object and a third object, wherein said first, second and third objects are separated from said area of interest by a distance t as measured along an axis;

said first and second objects are separated from one another by a distance $s_{min}$ that is smaller than both the distance separating the second and third objects and the distance separating the first and third objects;

wherein the greatest width of said first, second and third bodies is denoted by w; and wherein said x-ray beam forms a beam of inclination that is less than or equal to arctan(w/2t).

23. The method of claim 22, wherein said area of interest is entirely imaged only by x-ray beams that have an angle of inclination θ according to the relationship:

$$-\arctan(w/2t) \leq \theta \leq \arctan(w/2t).$$

24. The method of claim 22, wherein the angles of inclination that entirely image said area of interest are subtended by an angular range 2arctan(w/2t).

25. The method of claim 24, wherein adjacent locations produce x-ray beams that consecutive x-ray beams are angularly stepped relative to one another so that angle of inclination $\theta_i$ of an x-ray beam produced at the ith location, $P_i$, will be $\theta_i=\tan^{-1}(P_i/t)$, where $P_i=-w/2+iw/n$ and $n=w/s_{min}$=the total number of locations or steps.

26. The method of claim 6, wherein said item of interest is a circuit board.

27. The method of claim 26, wherein said object is solder.

28. The method of claim 6, wherein the number of locations is minimized while being of a sufficient number to entirely image said area of interest.

29. An apparatus for imaging a region of interest that is positioned on or within a test object that is obscured by a first obscuration body positioned on or within said test object but positioned outside said region of interest, comprising:

a radiation source that produces a beam of radiation;

a controller coupled to the radiation source, wherein the controller directs the beam of radiation towards predetermined locations of said test object, the predetermined locations being determined from an obscuration geometry of the first body relative to the area of interest.

30. The apparatus of claim 29, comprising a detector positioned to receive radiation that is transmitted through the test object from each of the predetermined locations and to produce images corresponding to each of the predetermined locations; and an imaging system that combines the images to produce an unobscured image of said region of interest.

31. The apparatus of claim 29, wherein said area of interest lies within a plane.

32. The apparatus of claim 29, wherein said object is positioned nearer to said source of radiation than said area of interest.

33. The apparatus of claim 29, wherein said item of interest is a circuit board.

34. The apparatus of claim 33, wherein said object is solder.

35. The apparatus of claim 29, wherein said source of radiation comprises an x-ray source and said radiation beam comprises an x-ray beam.

36. A method of imaging a region of interest that is positioned on or within a test object that is obscured by a first obscuration body positioned on or within said test object but positioned outside said region of interest, comprising:

generating a radiation beam;

directing the radiation beam to predetermined locations on the test object, wherein the predetermined locations are selected from a set of locations on the test object determined from an obscuration geometry of the first body relative to the area of interest.

37. The method of claim 36, comprising the step of for each of the predetermined locations, forming an image of said region of interest on or within the test object by detecting a portion of the radiation beam transmitted through the region of interest.

38. The method of claim 36, wherein the predetermined locations are determined from an obscuration geometry of the first body and a second obscuration body relative to the area of interest.

39. The method of claim 36, wherein said area of interest lies within a plane.

40. The method of claim 36, wherein said object is positioned nearer to said source of radiation than said area of interest.

41. The method of claim 36, wherein said object is separated from said area of interest by a distance t as measured along an axis;

said body having a width w; and wherein said radiation beam forms an angle of inclination that is greater than or equal to:

$$\theta_{max}=\arctan(w/2t).$$

42. The method of claim 41, wherein said area of interest is entirely imaged only by radiation beams that have an angle of inclination θ according to the relationship:

$$-\theta_{max} \leq \theta \leq \theta_{max}.$$

43. The method of claim 41, wherein the angles of inclination that entirely image said area of interest are subtended by an angular range 2θmax.

44. The method of claim 43, wherein adjacent locations produce x-ray beams that consecutive x-ray beams are angularly stepped relative to one another and the angular separation between consecutive x-ray beams differs by no more than $\Delta\theta=2\theta_{max}/n_{integer}$, where $n_{integer}$ is equal to the total number of locations.

45. The method of claim 36, comprising a second object, wherein said first and second objects are separated from said area of interest by a distance t as measured along an axis;

said second body having a width w that is greater than the width of said first object; and wherein said radiation beam forms a beam of inclination that is greater than or equal to:

$$\theta_{max}=\arctan(w/2t).$$

46. The method of claim 45, wherein said area of interest is entirely imaged only by radiation beams that have an angle of inclination θ according to the relationship:

$$-\theta_{max}\leq\theta\leq\theta_{max}.$$

47. The method of claim 45, wherein the angles of inclination that entirely image said area of interest are subtended by an angular range 2θmax.

48. The method of claim 47, wherein adjacent locations produce x-ray beams that consecutive x-ray beams are angularly stepped relative to one another and the angular separation between consecutive x-ray beams differs by no more than $\Delta\theta=2\theta_{max}/n_{integer}$, where $n_{integer}$ is equal to the total number of locations.

49. The method of claim 36, comprising a second object and a third object, wherein said first, second and third objects are separated from said area of interest by a distance t as measured along an axis;

said first and second objects are separated from one another by a distance $s_{min}$ that is smaller than both the distance separating the second and third objects and the distance separating the first and third objects;

wherein the greatest width of said first, second and third bodies is denoted by w; and wherein said radiation beam forms an angle of inclination that is greater than or equal to:

$$\theta_{max}=\arctan(w/2t).$$

50. The method of claim 49, wherein said area of interest is entirely imaged only by radiation beams that have an angle of inclination θ according to the relationship:

$$-\theta_{max}\leq\theta\leq\theta_{max}.$$

51. The method of claim 49, wherein the angles of inclination that entirely image said area of interest are subtended by an angular range 2θmax.

52. The method of claim 51, wherein adjacent locations produce radiation beams that are angularly separated from one another by no more than $\arctan(s_{min}/t)$.

53. The method of claim 36, comprising a second object and a third object, wherein said first, second and third objects are separated from said area of interest by a distance t as measured along an axis;

said first and second objects are separated from one another by a distance $s_{min}$ that is smaller than both the distance separating the second and third objects and the distance separating the first and third objects;

wherein the greatest width of said first, second and third bodies is denoted by w; and wherein said radiation beam forms an angle of inclination that is less than or equal to arctan(w/2t).

54. The method of claim 53, wherein said area of interest is entirely imaged only by x-ray beams that have an angle of inclination θ according to the relationship:

$$-\arctan(w/2t)\leq\theta\leq\arctan(w/2t).$$

55. The method of claim 53, wherein the angles of inclination that entirely image said area of interest are subtended by an angular range 2arctan(w/2t).

56. The method of claim 55, wherein adjacent locations produce x-ray beams that consecutive x-ray beams are angularly stepped relative to one another so that angle of inclination $\theta_i$ of an x-ray beam produced at the ith location, $P_i$, will be $\theta_i=\tan^{-1}(P_i/t)$ where $P_i=-w/2+iw/n$ and $n=w/s_{min}=$the total number of locations or steps.

57. The method of claim 36, wherein said item of interest is a circuit board.

58. The method of claim 57, wherein said object is solder.

59. The method of claim 36, wherein the number of locations is minimized while being of a sufficient number to entirely image said area of interest.

60. The method of claim 36, wherein said radiation beam comprises an x-ray beam.

* * * * *